(12) United States Patent
Ohashi et al.

(10) Patent No.: US 11,160,736 B2
(45) Date of Patent: Nov. 2, 2021

(54) LIP COSMETIC

(71) Applicant: SHISEIDO COMPANY, LTD., Tokyo (JP)

(72) Inventors: Shihoka Ohashi, Yokohama (JP); Yukiko Hiruma, Yokohama (JP); Takashi Matsuda, Yokohama (JP); Takashi Matsui, Yokohama (JP)

(73) Assignee: SHISEIDO COMPANY, LTD., Tokyo (JP)

(*) Notice: Subject to any disclaimer, the term of this patent is extended or adjusted under 35 U.S.C. 154(b) by 84 days.

(21) Appl. No.: 16/308,841

(22) PCT Filed: Nov. 18, 2016

(86) PCT No.: PCT/JP2016/084221
§ 371 (c)(1),
(2) Date: Dec. 11, 2018

(87) PCT Pub. No.: WO2017/216981
PCT Pub. Date: Dec. 21, 2017

(65) Prior Publication Data
US 2019/0192400 A1 Jun. 27, 2019

(30) Foreign Application Priority Data
Jun. 17, 2016 (JP) ................. 2016-120999

(51) Int. Cl.
A61K 8/37 (2006.01)
A61Q 1/04 (2006.01)
A61Q 1/06 (2006.01)
A61K 8/31 (2006.01)
A61K 8/895 (2006.01)
A61K 8/60 (2006.01)
A61K 8/41 (2006.01)
A61K 8/44 (2006.01)
A61K 8/81 (2006.01)
A61Q 17/04 (2006.01)
A61K 8/27 (2006.01)
A61K 8/29 (2006.01)
A61K 8/40 (2006.01)
A61K 8/02 (2006.01)
A61K 8/73 (2006.01)
A61K 8/92 (2006.01)

(52) U.S. Cl.
CPC .............. A61K 8/37 (2013.01); A61K 8/0229 (2013.01); A61K 8/27 (2013.01); A61K 8/29 (2013.01); A61K 8/31 (2013.01); A61K 8/40 (2013.01); A61K 8/41 (2013.01); A61K 8/44 (2013.01); A61K 8/445 (2013.01); A61K 8/60 (2013.01); A61K 8/602 (2013.01); A61K 8/732 (2013.01); A61K 8/8111 (2013.01); A61K 8/895 (2013.01); A61K 8/92 (2013.01); A61Q 1/04 (2013.01); A61Q 1/06 (2013.01); A61Q 17/04 (2013.01); A61K 2800/262 (2013.01); A61K 2800/48 (2013.01); A61K 2800/5922 (2013.01)

(58) Field of Classification Search
None
See application file for complete search history.

(56) References Cited

U.S. PATENT DOCUMENTS

2011/0182834 A1 7/2011 Do et al.

FOREIGN PATENT DOCUMENTS

| | | |
|---|---|---|
| EP | 1342463 | 9/2003 |
| JP | 2002-193749 | 7/2002 |
| JP | 2008-19200 | 1/2008 |
| JP | 2010-513541 | 4/2010 |
| JP | 2013-199452 | 10/2013 |
| JP | 2015-143195 | 8/2015 |
| JP | 2015-147740 | 8/2015 |
| WO | WO 2014/016349 | 1/2014 |

OTHER PUBLICATIONS

English translation of JP 2015-143195 (2015).*
PDF copy for Viscosity Unit (retrieval date: Oct. 8, 2020).*
PCT/JP2016/084221 International Search Report and Written Opinion, dated Jan. 24, 2017, 3 pages—English, 3 pages—Japanese.
PCT/JP2016/084221, Written Opinion dated Dec. 21, 2017, 5 pages—Japanese; 2 pages—English.
Extended European Search Report dated Nov. 15, 2019, 10 pages—English.
Hallstar@Octyl Isononanoate, Incl Name: Ethylhexyl Isononanoate, Product Cocde: HO14, Case #: 71566-49-9, Brand: Hallstar®, 2 pages—English, https://www.hallstarbeauty.com/product/hallstar-octyl-isononanoate/. dated Nov. 15, 2019.
Hal Global Network, Polyglyceryl-2, Triisostearate Risorex PGIS12, Incl Name: Polyglycerty-2 Triisostearate,, copyright © Kokyu Alcohol Kogyo Co., Ltd., 4 pages—English, https://www.hai-global.com/products/detail/37, dated Nov. 14, 2019.

(Continued)

Primary Examiner — Bong-Sook Baek
(74) Attorney, Agent, or Firm — Andrew F. Young; Nolte Lackenbach Siegel

(57) ABSTRACT

A lip cosmetic has a high transparency without giving unnatural whiteness and exerts a remarkable effect of ultraviolet ray protection over a broad wavelength range including the UVA and UVB regions. The lip cosmetic includes (A) at least 5% by mass of UV absorbers; wherein said (A) UV absorbers comprises (A1) at least one UV absorber selected from a group consisting of octocrylene, dimethicodiethylbenzalmalonate and diethylamino hydroxybenzoyl hexyl benzoate, and (A2) ethylhexyl methoxycinnamate; (B) a high-viscosity oil component in a range of 30% by mass to 70% by mass thereof; (C) a low-viscosity oil component in a range of 20% by mass to 40% by mass thereof, and (D) titanium dioxide and zinc oxide of which a total content is at most 0.5% by mass thereof; and wherein a sun-protection-factor (SPF) of the lip cosmetic is at least 20, and a critical wavelength thereof is at a shortest 370 nm.

8 Claims, No Drawings

(56) References Cited

OTHER PUBLICATIONS

Parchem, Chemical Search, Copyright © 2019 Parchem fine & specialty chemicals, Powered by ZIGIT, 10 pages—Engish, (http://www.zigit.mobi/Zigit). https://www.parchem.com/chemical-supplier-distribor/2-octyldodecannol-013670.aspx, dated Nov. 15, 2019.

* cited by examiner

LIP COSMETIC

CROSS REFERENCE TO RELATED APPLICATIONS

This application relates to and claims priority as a § 371 national phase, from PCT/JP2016/084221 filed Nov. 18, 2016, the entire contents of which are incorporated herein by reference, which in turn claims priority from JP 2016-120999 filed on Jun. 17, 2016.

TECHNICAL FIELD

The present invention relates to a lip cosmetic. More particularly, the present invention relates to a lip cosmetic that protects the lip from UV (ultra violet) ray exposure over a wide wavelength region from UVA to UVB and covers the lip with a high-transparent and non-whitish appearance result when applied thereto.

BACKGROUND ART

Protection of skin from harmful UV ray is one of the serious problems for skin care and body care, and various UV-protection skin care cosmetics capable of minimizing harmful impacts due to UV on skin have been developed. Whereas UVB having medium-wavelength of 290 to 320 nm is known to cause sunburn, inflammation and the like, UVA having long-wavelength of 320 to 400 nm also causes skin-aging i.e., skin photoaging. Therefore, various cosmetics capable of blocking UV of a wide wavelength and protecting essentially the skin from such broad UV spectrum have been proposed.

The outer horny layer of the lip is very thin, the lip has substantially no sebaceous gland, and the content of a natural moisturizing factor (NMF) component is little, so that the moisture thereof evaporates at a high-rate despite a less moisture content in the lip than the other regions of the skin, and as a result, the lips tend to dry and easily chap. In addition, an amount of melanin of the lip is small, so that the lip is more vulnerable to UV. Accordingly, it is significant how to protect the lips from external stimuli such as UV. In this regard, a UV absorber and a UV scattering agent become to generally be contained in a variety of lip cosmetics such as lip rouge and a lip balm.

Here, it should be paid more attention as to the safety particularly with regard to percutaneous absorption of the agents through the lip than the percutaneous absorption through the other regions because the lip has the aforementioned properties. Furthermore, since the cosmetic ingredient of the lip cosmetic is likely incorporated into the body through an oral route, so that further safety issue remains to be attainably solved. On the other hand, lip cosmetics such as a lip rouge are required to additionally have a cosmetic function as a makeup cosmetic, and hence, and particularly, it is important that such a lip cosmetic never provides unnaturally whitish appearance when applied to the lip.

Patent Document 1 discloses that when an oily cosmetic contains 2-ethylhexyl paramethoxycinnamate (A) and a benzophenone derivative (B) working as UV absorbers in combination with an oil component (C) and a viscosity adjusting component (D), and when its viscosity at 30° C. is set to 10000 mPa·s or more, the UV absorption level (i.e., SPF: Sun Protection Factor) is synergistically improved, and hence, higher UV protection effect (SPF) than that of a conventional product can be exhibited even if the content of the UV absorbers is reduced.

The SPF is, however, a benchmark value corresponding to protection level against mainly UVB, but the SPF cannot denote (reflect) the protection against UVA. In other words, even though the synergistic improvement as for the SPF, i.e., against UVB, can be obtained by employing the combination of the UV absorbers described in Patent Document 1, it has not been clearly disclosed that any protection against UVA provides as high as the level as against UVB. In addition, generally speaking, such a cosmetic most likely results in providing a white turbidity (which results in whitish appearance), if such an amount of the wax as disclosed in the examples of the Patent Document 1 is employed.

In order to improve the UV protection level for the UVA, in general, a substance having absorption in the UVA region is applied as a UV absorber, and an inorganic pigment such as titanium oxide and zinc oxide are applied as a UV scattering agent. In particular, whereas the UV scattering agent exhibits a UV protection effect by physically scattering UV and absorbing UV on the surface thereof, such agents cause a problem in which the agents provide an unnaturally whitish looking when applied to skin.

Patent Document 2 discloses a UV protection cosmetic containing (a) 3 to 15% by mass of one, two or more UV absorbers, (b) 10 to 22% by mass of zinc oxide having an average particle size of 35 to 80 nm, and optionally (c) 0 to 0.5% by mass of a white pigment. The content of the white pigment is lowered by containing a prescribed amount of zinc oxide having a large particle size and as a result, such a cosmetic does not look unnaturally white despite attaining SPF of 30 or more and a broad spectrum of a critical wavelength of 370 nm or more. Such a cosmetic is, however, only applicable to a general skin care cosmetic, and hence is insufficient to provide such a level of transparency required and significant for a lip cosmetic.

CITATION LIST

Patent Document
  Patent Document 1: JP-A 2013-199452
  Patent Document 2: JP-A 2014-040377

SUMMARY OF INVENTION

Technical Problem

Accordingly, an object of the present invention is to provide a lip cosmetic that is excellent in transparency without providing a whitish appearance (looking) despite a high and remarkable UV protection level over a wide wavelength spectrum in the range of UVA to UVB.

Solution to Problem

The present inventors earnestly made studies for solving the aforementioned problem, resulting in an unexpected finding, wherein when applying a specific combination of specific UV absorbers and oil contents having a different viscosity level from one another in a prescribed (predetermined) ratio, a lip cosmetic having a SPF of at least 20 and a broad spectrum as for the critical wavelength of 370 nm or longer is obtained even if the contents of zinc oxide and titanium dioxide, which cause whiteness, are much reduced, and thus, the present invention was accomplished.

Specifically, the present invention provides a lip cosmetic comprising (A) 5% by mass or more of UV absorber comprising (A1) at least one selected from the group consisting of octocrylene, dimethicodiethylbenzalmalonate and diethylamino hydroxybenzoyl hexyl benzoate, and (A2) ethylhexyl methoxycinnamate; (B) 30% by mass or more and 70% by mass or less of a high viscosity oil component; and (C) 20% by mass or more and 40% by mass or less of a low viscosity oil component, in which (D) a total content of titanium oxide (titanium dioxide) and zinc oxide is 0.5% by mass or less, and (E) SPF is 20 or more and a critical wavelength is 370 nm or more.

Advantageous Effects of Invention

The lip cosmetic of the present invention contains a specific combination of UV absorbers (A1) and (A2) described above and contains prescribed amounts of the high viscosity oil component (B) and the low viscosity oil component (C), and therefore, the contents of titanium oxide and zinc oxide having a UV scattering function can be suppressed. Accordingly, it has excellent UV protection capability over a wide wavelength region from UVA to UVB (namely, achieves a "broad spectrum"), and in addition, it is excellent in transparency and lips do not look white when it is applied. As a result, the lips can be satisfactorily protected from UV without impairing the makeup effect obtained as a lip rouge.

DESCRIPTION OF EMBODIMENT

A lip cosmetic of the present invention contains (A) UV absorbers, and the UV absorbers include (A1) at least one selected from the group consisting of octocrylene, dimethicodiethylbenzalmalonate and diethylamino hydroxybenzoyl hexyl benzoate, and (A2) ethylhexyl methoxycinnamate.

Octocrylene (synonym: 2-cyano-3,3-diphenylprop-2-enoic acid 2-ethylhexyl ester) is a diphenyl compound in the form of liquid at normal temperature.

Dimethicodiethylbenzalmalonate (synonym: polysilicone-15) is a silicone-modified compound in the form of liquid at normal temperature.

Diethylamino hydroxybenzoyl hexyl benzoate is a UV absorber in the form of a solid at normal temperature.

The lip cosmetic of the present invention comprises at least one ("component A1") selected from the group consisting of octocrylene, dimethicodiethylbenzalmalonate and diethylamino hydroxybenzoyl hexyl benzoate, as an essential component. If the component A1 is not contained, a sufficient UV protection effect cannot be obtained over a wide wavelength region from UVB to UVA.

Besides, the lip cosmetic of the present invention contains ethylhexyl methoxycinnamate ("component A2").

The ethylhexyl methoxycinnamate is a UV absorber in the form of a liquid at normal temperature and is widely used in cosmetics and the like.

The UV absorbers ("components A") used in the lip cosmetic of the present invention may include, an additional UV absorber, which is applicable to a cosmetic, in addition to the component A1 and the component A2.

Examples of the additional UV absorber includes, but are not limited to, benzophenone-based UV absorbers such as oxybenzone-3, oxybenzone-5 and oxybenzone-6, benzoic acid-based UV absorbers such as glyceryl para-aminobenzoate, salicylic acid-based UV absorbers such as ethylhexyl salicylate, benzoylmethane-based UV absorbers such as t-butyl methoxydibenzoylmethane, and benzotriazole-based UV absorbers.

The content of the UV absorbers (the components A) in the lip cosmetic of the present invention is 5% by mass or more, preferably 5.5% by mass or more, and more preferably 6% by mass or more. If the content is less than 5% by mass, sufficient UV protection level cannot be obtained. The upper limit of the content is not especially specified, but is generally 20% by mass or less, preferably 18% by mass or less, and more preferably 15% by mass or less.

The lip cosmetic of the present invention contains the high-viscosity oil component ("component (B)") and the low viscous oil component ("component (C)").

The high-viscosity oil component (B) of the present invention means an oil component having a viscosity, measured with a B type viscometer at 30° C., of 2,000 mPa·s or more, and the low-viscosity oil component (C) means an oil component having a viscosity, measured with a B type viscometer at 30° C., of less than 2,000 mPa·s.

The high-viscosity oil component (B) used in the present invention means a high-viscosity liquid oil component having such liquidity that the viscosity can be measured with a general viscometer, and does not include an oil component in the form of solid at normal temperature or having such hardness that the viscosity cannot be measured with a general viscometer (hereinafter referred to as a "wax").

Examples of the high-viscosity oil component (B) of the present invention include, but are not limited to, high-viscosity ester oils such as diisostearyl malate, sucrose tetraisostearate, triisostearin, and di(phytosteryl/octyldodecyl) lauroyl glutamate, high-viscosity hydrocarbon oils such as hydrogenated polyisobutene (hydrogenated isopolybutene), and high-viscosity silicone oils such as dimethicone. Among these, diisostearyl malate, sucrose tetraisostearate, triisostearin, di(phytosteryl/octyldodecyl) lauroyl glutamate and hydrogenated polyisobutene are preferably used.

Examples of the low-viscosity oil component (C) used in the present invention include, but are not limited to, low-viscosity ester oils such as diisopropyl sebacate, triethylhexanoin, isopropyl myristate and diethylhexyl succinate, lowviscosity hydrocarbon oils such as mineral oils and hydrogenated polydecene, and low viscosity silicone oils such as dimethicone. Among these, diisopropyl sebacate, triethylhexanoin, isopropyl myristate and diethylhexyl succinate are preferred.

It is noted that a UV absorber corresponding to the components A of the present invention is not included in the low viscosity oil component (C) or the high-viscosity oil component (B) even if it is an oil having a viscosity falling in either of the aforementioned ranges.

The content of the high-viscosity oil component (B) in the lip cosmetic of the present invention is 30% by mass or more, preferably 32% by mass or more, and more preferably 35% by mass or more. The upper limit of the content is not especially specified, but is generally 70% by mass or less, preferably 68% by mass or less, and more preferably 65% by mass or less.

The content of the low-viscosity oil component (C) in the lip cosmetic of the present invention is 20% by mass or more, preferably 22% by mass or more, and more preferably 25% by mass. The upper limit of the content is not especially specified, but is generally 40% by mass or less, preferably 35% by mass or less, and more preferably 30% by mass or less.

In the lip cosmetic of the present invention, a content ratio [(B)/(C)] of the high-viscosity oil component (B) to the low-viscosity oil component (C) is preferably in a range of 1 to 5, and particularly preferably in a range of 1 to 4.

If the components A to C are contained in the prescribed amounts, the lip cosmetic of the present invention exhibits excellent UV absorption level. Accordingly, the contents of titanium oxide and zinc oxide, which are widely used as UV scattering agents in cosmetics, can be suppressed, and hence unnatural whiteness derived from powders of these substances can be avoided.

The titanium oxide and the zinc oxide used in the present invention include not only pigment-grade powders used as white pigments but also fine particulate titanium oxide and particulate zinc oxide having a smaller average particle size.

The total content of the titanium oxide and the zinc oxide (also referred to as the "component D") in the lip cosmetic of the present invention is 0.5% by mass or less, preferably 0.3% by mass or less, and more preferably 0.1% by mass. Besides, the lip cosmetic of the present invention contains none of the titanium oxide and the zinc oxide in one aspect.

Owing to the aforementioned composition, the lip cosmetic of the present invention has characteristically a SPF of 20 or more and a critical wavelength of 370 nm or more even if the contents of titanium oxide and zinc oxide serving as UV scattering agents are reduced. In other words, such a lip cosmetic can provide well-balanced UV protection over a wide wavelength region from UVA to UVB.

Here, a value of "SPF (Sun Protection Factor)" in the present invention is a value measured using an SPF measuring apparatus "SPF MASTER®" unless otherwise specified.

A critical wavelength is an index introduced in the Final Rule of U. S. Food and Drug Administration (FDA) published in June 2011, and a critical wavelength ($\lambda c$) is a value defined by the following expression:

[Expression 1]

$$\int_{290}^{\lambda c} A(\lambda)d\lambda = 0.9 \int_{290}^{400} A(\lambda)d\lambda$$

Briefly speaking, a UV protection cosmetic is applied onto a prescribed plate, followed by irradiation with light of 4 MED, and then an absorption spectrum is measured. Assuming that an integral value of absorbance at 290 nm to 400 nm in the absorption spectrum is 100%, a wavelength, from 290 nm in increments of 1 nm, at which an integrated value of the absorbance reaches 90% is defined as the critical wavelength ($\lambda c$). In the Final Rule, merely a product having the critical wavelength ($\lambda c$) of 370 nm or more is allowed to claim a "broad spectrum" product in the market.

The lip cosmetic of the present invention may comprise, in addition to the components A to D described above, other optional components that can be generally contained in lip cosmetics such as lipsticks and lip rouges (in the form of paste or liquid) as long as the effects of the present invention are not impaired.

In particular, if the lip cosmetic of the present invention is provided in the form of a solid stick or a solid paste, a wax (defined as above) or an oil thickener (a gelling agent) is preferably contained.

Examples of the wax that can be contained in the present invention include solid fats and oils, waxes, hydrocarbons and higher alcohols. Specific examples include solid fats and oils such as haze wax, cacao butter and hydrogenated castor oil; waxes such as carnauba wax, beeswax, candelilla wax and jojoba wax; hydrocarbon waxes such as polyethylene wax, paraffin wax, ceresin and microcrystalline wax; higher alcohols such as behenyl alcohol, cetanol and batyl alcohol; and silicon waxes. Among these, the hydrocarbon waxes such as polyethylene wax, paraffin wax and microcrystalline wax are particularly preferably contained because solidifiability (or formability) in forming a stick shape and whiteness prevention can be improved when they are contained.

The content of the wax in the lip cosmetic of the present invention is preferably 4 to 13% by mass and more preferably 7 to 10% by mass generally based on the total amount of the cosmetic.

Examples of the oil thickener (the gelling agent) that can be contained in the present invention include dextrin fatty acid esters, glycerin fatty acid esters and organic modified clay minerals. Examples of the dextrin fatty acid esters include dextrin myristate, dextrin palmitate and dextrin (palmitate/2-ethylhexanoate). Examples of the glycerin fatty acid esters include glyceryl behenate, glyceryl octastearate and glyceryl eicosanoate.

The content of the oil thickener in the cosmetic in the shape of a solid paste is 2.5% by mass to 15% by mass, preferably 3.0% by mass to 12% by mass, and 4.0% by mass to 10% by mass.

Examples of the other optional components include, but are not limited to, water-soluble polymers, oil-soluble polymers, lower alcohols, higher alcohols, surface active agents, powder components (including pigments) excluding titanium oxide and zinc oxide, colorants and drugs.

Examples of the water-soluble polymers include homopolymers or copolymers of 2-acrylamide-2-methylpropane sulfonic acid (hereinafter abbreviated as "AMPS"). Examples of the copolymers include those with comonomers such as vinyl pyrrolidone, acrylic acid amide, sodium acrylate and hydroxyethyl acrylate. Specifically, examples include AMPS homopolymers, vinyl pyrrolidone/AMPS copolymers, dimethylacrylamide/AMPS copolymers, acrylic acid amide/AMPS copolymers and sodium acrylate/AMPS copolymers.

Other examples include carboxyvinyl polymers, ammonium polyacrylate, sodium polyacrylate, sodium acrylate/alkyl acrylate/sodium methacrylate/alkyl methacrylate copolymers, carrageenan, pectin, mannan, curdlan, chondroitin sulfate, starch, glycogen, gum arabic, sodium hyaluronate, gum tragacanth, gum xanthan, mucoitinsulfuric acid, hydroxyethyl guar gum, carboxymethyl guar gum, guar gum, dextran, keratosulfate, locust bean gum, succinoglucan, chitin, chitosan, carboxymethyl chitin, and agar.

Examples of the oil-soluble polymers include trimethylsiloxysilicate, alkyl modified silicone, polyamide modified silicone, dimethicone crosspolymers, (dimethicone/vinyldimethicone) crosspolymers and polymethylsilsesquioxane.

Examples of the surfactant (surface active agents) include anionic, cationic, nonionic and amphoteric surfactant, and include silicone-based and hydrocarbon-based surfactant.

Examples of the powder components, other than titanium oxide and zinc oxide, include color pigments and extender pigments such as barium sulfate, iron oxide, talc, mica, sericite, kaolin, mica titanium, ultramarine, chromium oxide, chromium hydroxide, silica and cerium oxide. Besides, nylon-based or acrylic-based polymer spherical powders, silica powders, silicone powders and the like may be contained if necessary.

The lip cosmetic of the present invention is preferably in the form of an oily cosmetic containing no water or a small amount of water (for example, 1.5% by mass or less). The specific form can be a solid form (stick or paste), a cream or a gel, and the lip cosmetic is preferably in a stick or a solid paste.

EXAMPLES

Now, the present invention will be described in more details with reference to examples, and it is noted that the present invention is not limited to these examples. A content of a component mentioned below are expressed in unit of % by mass based on the total amount of a system in which the component is contained unless otherwise specified.

Samples of lip cosmetics were prepared in accordance with formulations listed in Tables 1 to 4 below. Subsequently, each of the prepared samples was subjected to measurement for an SPF value and a critical wavelength.

Besides, "solidifiability", "glossiness and fit feeling (fitting and comfortable sensation)" and "whiteness when applied (whitish appearance)" of each sample were evaluated based on the following criteria.

(1) Solidifiability

Solidifiability in solidifying each sample in accordance with a usual method employed for a solid stick cosmetic or a paste cosmetic was evaluated.

A: The sample solidifies without any problem.

B: The sample solidifies but the obtained solid sample crumbles easily.

C: The sample never solidifies.

(2) Glossiness and Fit-feeling (fitting-and-comfortable sensation)

Expert panelists evaluate the terms while applying each sample.

A: Excellent in glossiness and fit-feeling

B: Poor in glossiness and fit-feeling (3) Whitish appearance when Applied Expert panelists evaluate a whitish appearance when applying each sample to lips.

A: No whitish appearance on the lips

B: Unnatural whitish appearance.

The respective evaluation results are shown in Tables 1 to 4.

TABLE 1

| Name of Ingredient | Example 1 | Example 2 | Example 3 | Example 4 | Example 5 | Example 6 | Example 7 | Example 8 |
|---|---|---|---|---|---|---|---|---|
| Polyethylene wax | 10.0 | 10.0 | 4.0 | 5.0 | 8.0 | 9.0 | 10.0 | 4.0 |
| Microcrystalline wax | — | — | 4.0 | 5.0 | 1.0 | — | — | 4.0 |
| Hydrogenated polyisobutene | 5.0 | 5.0 | 10.0 | 10.0 | 15.0 | 15.0 | 15.0 | 15.0 |
| Diisostearyl malate | 56.5 | 56.5 | 27.9 | 27.7 | 33.9 | 32.4 | 32.4 | 32.4 |
| Triethylhexanoin | 10.0 | 10.0 | 25.0 | 30.0 | 25.0 | 25.0 | 25.0 | 25.0 |
| Diisopropyl sebacate | 10.0 | 10.0 | — | — | — | — | — | — |
| Oxybenzone-3 | — | — | 3.0 | 3.0 | 2.5 | 2.5 | 2.5 | 2.5 |
| t-Butyl methoxydibenzoylmethane | — | — | 1.0 | 1.0 | 2.0 | 1.0 | 1.0 | 1.0 |
| Diethylamino hydroxybenzoyl hexyl benzoate | 1.0 | 0.5 | — | — | — | — | — | — |
| Dimethicodiethylbenzal malonate | — | — | 10.0 | 8.0 | — | — | — | — |
| Octocrylene | — | — | — | — | 5.0 | 5.0 | 5.0 | 5.0 |
| Ethylhexyl methoxycinnamate | 5.0 | 5.0 | 8.0 | 8.0 | 5.0 | 5.0 | 5.0 | 5.0 |
| Polyglyceryl-2 diisostearate | 1.0 | 1.0 | 1.0 | 1.0 | 1.0 | 1.0 | 1.0 | 1.0 |
| Water | 1.0 | 1.0 | 1.1 | 1.1 | 1.1 | 1.1 | 1.1 | 1.1 |
| Iron oxide | 0.1 | — | — | 0.1 | 0.1 | — | — | — |
| Red No. 202 | — | 0.5 | 2.0 | — | — | 1.0 | 1.0 | 1.0 |
| Butylene glycol | q.s. | q.s. | q.s. | q.s. | q.s. | q.s. | q.s. | q.s. |
| Antioxidant | q.s. | q.s. | q.s. | q.s. | q.s. | q.s. | q.s. | q.s. |
| Perfume | q.s. | q.s. | q.s. | q.s. | q.s. | q.s. | q.s. | q.s. |
| Total | 100 | 100 | 100 | 100 | 100 | 100 | 100 | 100 |
| [(B)/(C)] | 3.1 | 3.1 | 1.5 | 1.3 | 2.0 | 1.9 | 1.9 | 1.9 |
| Measured SPF value | 25 | 22 | 32 | 28 | 25 | 22 | 22 | 32 |
| Measured Critical Wavelength (nm) | 371 | 371 | 373 | 373 | 371 | 372 | 372 | 373 |
| Stick Solidifiability | A | A | A | A | A | A | A | A |
| Glossiness and Fit-Feeling | A | A | A | A | A | A | A | A |
| Whiteness when Applied | A | A | A | A | A | A | A | A |

"q.s." stands for quantum sufficit.

TABLE 2

| Name of Ingredient | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|
| Polyethylene wax | 10.0 | 10.0 | 4.0 | 4.0 | 8.0 | 8.0 | 7.0 | 9 |
| Microcrystalline wax | — | — | 4.0 | 2.0 | 1.0 | 1.0 | 1.0 | 1 |
| Hydrogenated polyisobutene | 5.0 | 10.0 | 10.0 | 15.0 | 1.0 | 15.0 | 1.0 | 20.0 |
| Diisostearyl malate | 57.5 | 38.4 | 37.9 | 39.9 | 19.9 | 39.9 | 32.0 | 35.0 |
| Triethylhexanoin | 10.0 | 25.0 | 25.0 | 25.0 | 5.0 | 25.0 | 25.0 | 5 |

TABLE 2-continued

| Name of Ingredient | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|
| Diisopropyl sebacate | 10.0 | — | — | — | 40.0 | — | 20.0 | — |
| Oxybenzone-3 | — | 3.0 | 3.0 | 2.5 | 2.5 | 2.5 | 2.5 | 2.5 |
| t-Butyl methoxydibenzoylmethane | — | 0.5 | 1.0 | 1.0 | 1.0 | 1.0 | 1.0 | 1.0 |
| Diethylamino hydroxybenzoyl hexyl benzoate | — | — | — | — | 0.5 | — | — | — |
| Dimethicodiethylbenzal malonate | — | — | — | — | — | — | — | — |
| Octocrylene | — | — | — | — | — | — | 2.0 | 5.0 |
| Ethylhexyl methoxycinnamate | 5.0 | 8.0 | 8.0 | 5.0 | 5.0 | 5.0 | 5.0 | 5.0 |
| Polyglyceryl-2 diisostearate | 1.0 | 1.0 | 1.0 | 1.0 | 1.0 | 1.0 | 1.0 | 1.0 |
| Water | 1.0 | 1.1 | 1.1 | 1.1 | 1.1 | 1.1 | 1.1 | 1.1 |
| Iron oxide | 0.4 | — | — | 0.5 | 0.5 | 0.1 | 0.5 | 0.5 |
| Red No. 202 | — | 1.0 | 3.0 | — | — | — | — | — |
| Butylene glycol | q.s. | q.s. | q.s. | q.s. | q.s. | q.s. | q.s. | q.s. |
| Antioxidant | q.s. | q.s. | q.s. | q.s. | q.s. | q.s. | q.s. | q.s. |
| Perfume | q.s. | q.s. | q.s. | q.s. | q.s. | q.s. | q.s. | q.s. |
| Total | 100 | 100 | 100 | 100 | 100 | 100 | 100 | 100 |
| [(B)/(C)] | 3.1 | 1.9 | 1.9 | 2.2 | 0.5 | 2.2 | 0.7 | 11 |
| Measured SPF value | 16 | 17 | 18 | 15 | 18 | 15 | 15 | 22 |
| Measured Critical Wavelength (nm) | 368 | 360 | 370 | 365 | 360 | 365 | 365 | 372 |
| Stick Solidifiability | A | A | A | A | C | B | A | A |
| Glossiness and Fit-Feeling | A | A | A | A | A | A | B | B |
| Whiteness when Applied | A | A | A | A | A | A | A | A |

"—" denotes not-contained.

It is obvious from the results of lip rouges in the shape of a solid stick shown in Tables 1 and 2 with respect to Examples 1 to 8, in which a combination of the component A1 and the component A2 as the UV absorbers and the high-viscosity oil component and the low-viscosity oil component in prescribed amounts are contained, that the high SPF value and the critical wavelength of 370 nm or more are attained, all the evaluation level regarding the solidifiability, the glossiness and the fit-feeling (fitting-and-comfortable sensation), and the applied appearance free from whiteness are excellent. On the contrary, in Comparative Examples 1 to 4 and 6, in which the component A1 was not contained, the SPF is lower than 20, and the critical wavelength is not over 370 nm. In Comparative Example 5, in which the content of the high-viscosity oil component was lower than 30% by mass, the sample fails to form (be solidified) a stick. Besides, in Comparative Example 7, in which the content of the low-viscosity oil component is higher than 40% by mass and the content ratio ((B)/(C)) of the high-viscosity oil component (excluding a wax) to the low-viscosity oil component is lower than 1, and in Comparative Example 8, in which the content of the low-viscosity oil component is lower than 20% by mass and the content ratio ((B)/(C)) higher than 5, the evaluations of the samples are poor in the glossiness and the fit feeling.

TABLE 3

| Name of Ingredient | Example 9 | Example 10 | Example 11 | Reference Example 1 | Reference Example 2 | Reference Example 3 | Example 12 |
|---|---|---|---|---|---|---|---|
| Polyethylene wax | 6.0 | 9.0 | 5.0 | — | — | — | 10.0 |
| Microcrystalline wax | 2.0 | — | 5.0 | — | — | — | — |
| Beeswax | — | — | — | 10.0 | — | 7.0 | — |
| Carnauba wax | — | — | — | — | 15.0 | 7.0 | — |
| Hydrogenated polyisobutene | 5.0 | 5.0 | 10.0 | 5.0 | 5.0 | 10.0 | 10.0 |
| Diisostearyl malate | 56.5 | 47.5 | 27.9 | 47.5 | 41.5 | 21.9 | 21.9 |
| Triethylhexanoin | 10.0 | 10.0 | 25.0 | 10.0 | 10.0 | 25.0 | 25.0 |
| Diisopropyl sebacate | 10.0 | 10.0 | — | 10.0 | 10.0 | — | — |
| Oxybenzone-3 | — | — | 3.0 | — | — | 3.0 | — |
| t-Butyl methoxydibenzoylmethane | — | — | 1.0 | — | — | 1.0 | — |
| Diethylamino hydroxybenzoyl hexyl benzoate | 1.0 | 0.5 | — | 1.0 | 0.5 | — | 1.0 |
| Dimethicodiethylbenzal malonate | — | — | 10.0 | — | — | 10.0 | 10 |

TABLE 3-continued

| Name of Ingredient | Example 9 | Example 10 | Example 11 | Reference Example 1 | Reference Example 2 | Reference Example 3 | Example 12 |
|---|---|---|---|---|---|---|---|
| Octocrylene | — | — | — | — | — | — | — |
| Ethylhexyl methoxycinnamate | 5.0 | 5.0 | 8.0 | 5.0 | 5.0 | 8.0 | 8.0 |
| Polyglyceryl-2 diisostearate | 1.0 | 1.0 | 1.0 | 1.0 | 1.0 | 1.0 | 1.0 |
| Water | 1.0 | 1.0 | 1.1 | 1.0 | 1.1 | 1.1 | 1.0 |
| Iron oxide | 0.5 | — | — | 0.5 | — | — | 0.1 |
| Red No. 202 | — | 5.0 | 1.0 | — | 5.0 | 2.0 | — |
| Butylene glycol | q.s. | q.s. | q.s. | q.s. | q.s. | q.s. | q.s. |
| Antioxidant | q.s. | q.s. | q.s. | q.s. | q.s. | q.s. | q.s. |
| Perfume | q.s. | q.s. | q.s. | q.s. | q.s. | q.s. | q.s. |
| Total | 100 | 100 | 100 | 100 | 100 | 100 | 100 |
| [(B)/(C)] | 3.1 | 2.6 | 1.5 | 2.6 | 2.3 | 1.3 | 3.1 |
| Measured SPF value | 25 | 22 | 32 | 25 | 22 | 32 | 32 |
| Measured Critical Wavelength (nm) | 371 | 371 | 373 | 371 | 371 | 373 | 370 |
| Stick Solidifiability | A | A | A | B | B | B | A |
| Glossiness and Fit-Feeling | A | A | A | A | A | A | A |
| Whiteness of the Appearance | A | A | A | B | B | B | A |

In the results of lip rouges also in the shape of a solid stick shown in Table 3, in Reference Examples 1 to 3, in which waxes used in the samples of Examples 9 to 11 excellent in all the evaluation items were all replaced with waxes excluding hydrocarbon waxes, the solidifiability in forming a stick is lowered, and whiteness of the applied appearance is slightly conspicuous. Incidentally, it is presumed that the whiteness of the appearance is caused also because the content of the wax is larger than 13% by mass (in References Examples 2 and 3). Accordingly, in producing a stick-shaped cosmetic, it is preferable to selectively contain a hydrocarbon-based wax in a content of 13% by mass or less.

TABLE 4

| Name of Ingredient | Example 13 | Example 14 | Example 15 | Reference Example 4 | Reference Example 5 |
|---|---|---|---|---|---|
| Microcrystalline wax | — | — | 10.0 | 20.0 | — |
| Dextrin palmitate | 10.0 | 5.0 | — | — | 2.0 |
| Hydrogenated polyisobutene | 5.0 | 5.0 | 10.0 | 5.0 | 10.0 |
| Diisostearyl malate | 56.5 | 57.5 | 21.9 | 45.5 | 31.9 |
| Triethylhexanoin | 10.0 | 10.0 | 25.0 | 10.0 | 25.0 |
| Diisopropyl sebacate | 10.0 | 10.0 | — | 10.0 | — |
| Oxybenzone-3 | — | — | — | — | 3.0 |
| t-Butyl methoxydibenzoylmethane | — | — | — | — | 1.0 |
| Diethylamino hydroxybenzoyl hexyl benzoate | 1.0 | 0.5 | 1.0 | 1.0 | — |
| Dimethicodiethylbenzalmalonate | — | — | 10.0 | — | 10.0 |
| Octocrylene | — | — | — | — | — |
| Ethylhexyl methoxycinnamate | 5.0 | 5.0 | 8.0 | 5.0 | 8.0 |
| Polyglyceryl-2 diisostearate | 1.0 | 1.0 | 1.0 | 1.0 | 1.0 |
| Water | 1.0 | 1.0 | 1.1 | 1.0 | 1.1 |
| Iron oxide | 0.4 | — | — | 0.5 | — |
| Red No. 202 | — | 1.0 | 5.0 | — | 5.0 |
| Butylene glycol | q.s. | q.s. | q.s. | q.s. | q.s. |
| Antioxidant | q.s. | q.s. | q.s. | q.s. | q.s. |
| Perfume | q.s. | q.s. | q.s. | q.s. | q.s. |
| Total | 100 | 100 | 100 | 100 | 100 |
| [(B)/(C)] | 3.1 | 3.1 | 1.3 | 2.5 | 1.7 |
| Measured SPF value | 25 | 22 | 32 | 25 | 32 |
| Measured Critical Wavelength (nm) | 371 | 371 | 370 | 371 | 373 |
| Paste Solidifiability | A | A | A | A | B |
| Glossiness and Fit Feeling | A | A | A | A | A |
| Whiteness of the Appearance | A | A | A | B | B |

In the results of lip cosmetics in the shape of a solid paste shown in Table 4, the type or the content of a wax or an oil thickener used in each of the samples of Examples 13 to 15 excellent in all the evaluation items are different, and in Reference Example 4 in which a wax was contained in a content larger than 13% by mass, the whiteness is slightly conspicuous, and in Reference Example 5 in which the content of the oil thickener is 2% by mass, the solidifiability is slightly insufficient, and the whiteness of the appearance is conspicuous. In other words, it is preferable to formulate an oil 2.5% by mass or more of an oil thickener to make a lip cosmetic in the shape of a solid paste.

The following is another example of the formulation of a makeup cosmetic according to the present invention. Also, the following makeup cosmetic attains a bright fluorescent color and transparency.

Formulation Example 1: Lip Gloss

| | Ingredients | Content (% by mass) |
|---|---|---|
| 1. | Triethylhexanoin | 10.0 |
| 2. | Hydrogenated isopolybutene | 5.0 |
| 3. | Diisostearyl malate | 56.5 |
| 4. | Dextrin palmitate | 10.0 |
| 5. | Diisopropyl sebacate | 10.0 |
| 6. | Diethylamino hydroxybenzoyl hexyl benzoate | 1.0 |
| 7. | Ethylhexyl methoxycinnamate | 5.0 |

-continued

| | Ingredients | Content (% by mass) |
|---|---|---|
| 8. | Iron oxide | 0.1 |
| 9. | Red No. 202 | 0.1 |
| 10. | Tocopherol | q.s. |
| 11. | Perfume | q.s. |
| 12. | Diphenylsiloxy phenyl trimethicone | balance |

The invention claimed is:

1. A lip cosmetic, comprising:
(A) at least 5% by mass of ultra-violet ray absorbers; wherein said (A) ultra-violet ray absorbers comprise:
 (A1) at least one ultra-violet ray absorber selected from the group consisting of octocrylene, dimethicodiethylbenzalmalonate and diethylamino hydroxybenzoyl hexyl benzoate, and
 (A2) ethylhexyl methoxycinnamate;
(B) a high-viscosity oil component in a range of 30% by mass to 70% by mass;
 wherein the high-viscosity oil component (B) is one or more selected from diisostearyl malate, sucrose tetraisostearate, triisostearin, and hydrogenated polyisobutene;
(C) a low-viscosity oil component in a range of 20% by mass to 40% by mass;
 wherein the low-viscosity oil component (C) has a viscosity, measured with a B type viscometer at 30° C., of less than 2,000 mPa·s and is one or more selected from ester oils, hydrocarbon oils, and silicone oils; and
(D) titanium dioxide, or zinc oxide, or a mixture of both, in a range of 0 to 0.5% by mass;
wherein the mass ratio between said high-viscosity oil component (B) and said low-viscosity oil component (C), expressed by (B)/(C), is in the range of 1.3 to 3.5; and
wherein a sun-protection-factor (SPF) of said lip cosmetic is at least 20, and a critical wavelength thereof is at shortest 370 nm.

2. The lip cosmetic, according to claim 1, wherein: said low-viscosity oil component (C) comprises: at least one selected from the group consisting of diisopropyl sebacate, triethylhexanoin, isopropyl myristate and diethylhexyl succinate.

3. The lip cosmetic, according to claim 1, further comprising:
at least one wax, wherein said lip cosmetic is a solid stick.

4. The lip cosmetic, according to claim 3, wherein a content of said wax is in a range of 4 to 13% by mass based on said lip cosmetic.

5. The lip cosmetic, according to claim 3, wherein: said wax further comprises at least one hydrocarbon wax selected from the group consisting of polyethylene wax, paraffin wax and microcrystalline wax.

6. The lip cosmetic, according to claim 1, further comprising:
at least one oil thickener, wherein said lip cosmetic is a solid paste.

7. The lip cosmetic, according to claim 6, wherein:
said oil thickener is in a range of 2.5 to 15% by mass based on said lip cosmetic.

8. The lip cosmetic according, to claim 6, wherein:
the oil thickener comprises a dextrin fatty acid ester.

* * * * *